US011607538B2

(12) United States Patent
Shepard et al.

(10) Patent No.: US 11,607,538 B2
(45) Date of Patent: Mar. 21, 2023

(54) FULLY IMPLANTED, WIRELESS, FLEXIBLE CMOS SURFACE RECORDING DEVICE

(71) Applicant: The Trustees of Columbia University in the City of New York, New York, NY (US)

(72) Inventors: Kenneth Shepard, Ossining, NY (US); David Tsai, New York, NY (US); Nanyu Zeng, Troy, NY (US); Taesung Jung, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 658 days.

(21) Appl. No.: 16/604,348

(22) PCT Filed: Apr. 10, 2018

(86) PCT No.: PCT/US2018/026901
§ 371 (c)(1),
(2) Date: Oct. 10, 2019

(87) PCT Pub. No.: WO2019/018020
PCT Pub. Date: Jan. 24, 2019

(65) Prior Publication Data
US 2020/0155828 A1    May 21, 2020

Related U.S. Application Data

(60) Provisional application No. 62/483,585, filed on Apr. 10, 2017.

(51) Int. Cl.
*A61N 1/05* (2006.01)
*A61B 5/00* (2006.01)
(Continued)

(52) U.S. Cl.
CPC .......... *A61N 1/0534* (2013.01); *A61B 5/0031* (2013.01); *A61N 1/3787* (2013.01); *A61N 1/37264* (2013.01); *A61B 2562/046* (2013.01)

(58) Field of Classification Search
CPC .............. A61N 1/0534; A61N 1/37264; A61N 1/3787; A61B 5/0031; A61B 2562/046; A61B 5/291
See application file for complete search history.

(56) References Cited

U.S. PATENT DOCUMENTS 6,044,301 A * 3/2000 Hartlaub ............ A61N 1/37258
607/31
9,907,950 B1 * 3/2018 Perryman ............ A61N 1/3756
(Continued)

FOREIGN PATENT DOCUMENTS

| DE | 4244646 | 6/1994 | |
|----|---------|--------|---|
| WO | WO 2017/035530 | 3/2017 | |
| WO | WO-2017035530 A1 * | 3/2017 | ........... A61B 5/0031 |

OTHER PUBLICATIONS

Rituerto et al. "Fretting Corrosion of Hafnium in Simulated Body Fluids," Tribology International, vol. 75, pp. 10-15 (Jul. 2014).
(Continued)

*Primary Examiner* — Catherine M Voorhees
(74) *Attorney, Agent, or Firm* — Hunton Andrews Kurth LLP

(57) ABSTRACT

A fully implanted integrated, wireless, flexible CMOS chip for long-term recording and stimulation of the brain in vivo and methods of manufacturing thereof are provided. The chip is an entire biocompatible system and can include the dense surface electrode array, the underlying CMOS integrated circuit architecture, integrated wireless powering and telemetry. Furthermore, miniaturization through manufacturing, permits implantation of the chip under the skull and other regions of interest with no wires or connections.
(Continued)

Furthermore, these devices and systems can operate under a dual modality such as to be able to record and stimulate the surface of the brain and/or tissue in which they have been implanted.

22 Claims, 13 Drawing Sheets

(51) Int. Cl.
 *A61N 1/378* (2006.01)
 *A61N 1/372* (2006.01)

(56) References Cited

U.S. PATENT DOCUMENTS

| | | | |
|---|---|---|---|
| 2014/0275929 A1* | 9/2014 | Chen ................ | H01L 24/92 |
| | | | 438/618 |
| 2014/0353791 A1* | 12/2014 | Jain ................ | A61B 5/6846 |
| | | | 257/434 |
| 2015/0157862 A1 | 6/2015 | Greenberg et al. | |
| 2016/0073920 A1* | 3/2016 | Kassegne ............. | A61B 5/24 |
| | | | 430/319 |
| 2018/0117318 A1* | 5/2018 | Milekovic ........... | A61B 5/0036 |

OTHER PUBLICATIONS

International Search Report and Written Opinion for International Patent Appliation No. PCT/US2018/026901 dated Jan. 8, 2019.

\* cited by examiner

FULLY IMPLANTED, WIRELESS, FLEXIBLE CMOS SURFACE RECORDING DEVICE

CROSS REFERENCE TO REPLATED APPLICATION(S)

The present application relates to and claims priority from International Patent Application No. PCT/US2018/026901 filed 10, 2018 which published as International Publication No, WO 2019/018020 on Jan. 24, 2019, and from U.S. Provisional Patent Application No. 62/483,585, filed on Apr. 10, 2017, the entire disclosures of which are incorporated herein by reference.

STATEMENT REGARDING FEDERALLY SPONSORED RESEARCH

This invention was made with government support under N66001-17-C-4002 awarded by the Defense Advanced Research Projects Agency (DARPA). The government has certain rights in the invention.

BACKGROUND

Certain in vivo neural recording devices take the form of low-density electrode arrays that require wires to be run outside of the body, making these arrays cumbersome and prone to infection. The information acquired from these systems can be invaluable to the advancement of the understanding of the brain and in the development of neural prosthetic devices and brain-machine interfaces. However, in order to provide a better understanding of neuroscience and clinical neurology, there is a need for long-term implantable neural recording devices that offer many recording channels and a safe mode of data transmission.

One method for recording brain activity involves the use of electrophysiology. Electrodes permit both recording and stimulation, opening an avenue not just for understanding neural behavior but for actuating neural responses. Certain electrode arrays can require running wires through the skull and displace significant tissue volume, increasing inflammatory response. Scarring and gliosis is also increased by the rigid nature of certain electrodes and the rigid attachment of these electrodes to the skull.

In addition, microelectrode arrays can be fabricated using modern microelectronics processes, specifically complementary metal-oxide-semiconductor (CMOS) processes. Large numbers of surface recording and stimulating electrodes can be integrated with circuitry to condition recorded signals in an in vitro setting.

Accordingly, there is a need for effective and reliable long-term, multichannel, implantable recording devices for acquiring neuronal recordings.

SUMMARY

An integrated, wireless chip for long-term recording and stimulation of the brain in vivo and methods of manufacturing thereof are provided. In some embodiments an implantable neural recording and stimulation device is provided including a flexible and thinned CMOS chip, an array of electrodes integrated into the CMOS chip that are capable of recording one or more analog signals and configured to operate in a dual operation mode, and a microcontroller coupled to the array of electrodes that controls switching of the array of electrodes between a first operation mode and a second operation mode. In some embodiments, the chip is an entire system and can include the dense surface electrode array, the underlying CMOS integrated circuit architecture, integrated wireless powering and telemetry. Furthermore, miniaturization through manufacturing can permit implantation of the chip under the skull with no wires or connections.

Furthermore, in some embodiments, a fully implanted, wireless system for long-term surface recording and stimulation of the brain in vivo is provided whereby this device can take the form of a monolithically constructed CMOS integrated circuit, which can contain a high-density microelectrode array, on-chip data converters, antennae for transmitting and receiving data, and an antenna for receiving power or any other suitable circuit.

Additionally, through post-processing for example during manufacturing, the chip can be thinned to thicknesses of less than 15 μm as to be pliable enough to conform to the surface of the brain or any other suitable tissue while simultaneous reducing displacing the tissue. In some embodiments, the chip can be encapsulated after thinning.

The disclosed subject matter provides for devices and systems that can operate under a dual modality such as to be able to record and stimulate the surface of the brain and/or tissue in which they have been implanted. In addition, the density of the electrode arrays can exceed modern surface electrode arrays by several orders of magnitude e.g., 2 or more. This density can be achieved without sacrificing the quality of recordings.

Certain electrode arrays are wired to any necessary hardware components such as amplifiers and data converters. In the disclosed subject matter, electrodes, amplifiers, and data converters can be monolithically integrated. Antennae can also fully integrated to enable wirelessly powering and telemetry. The thinning process provides for flexibility to be achieved in the device.

Figure 1A:
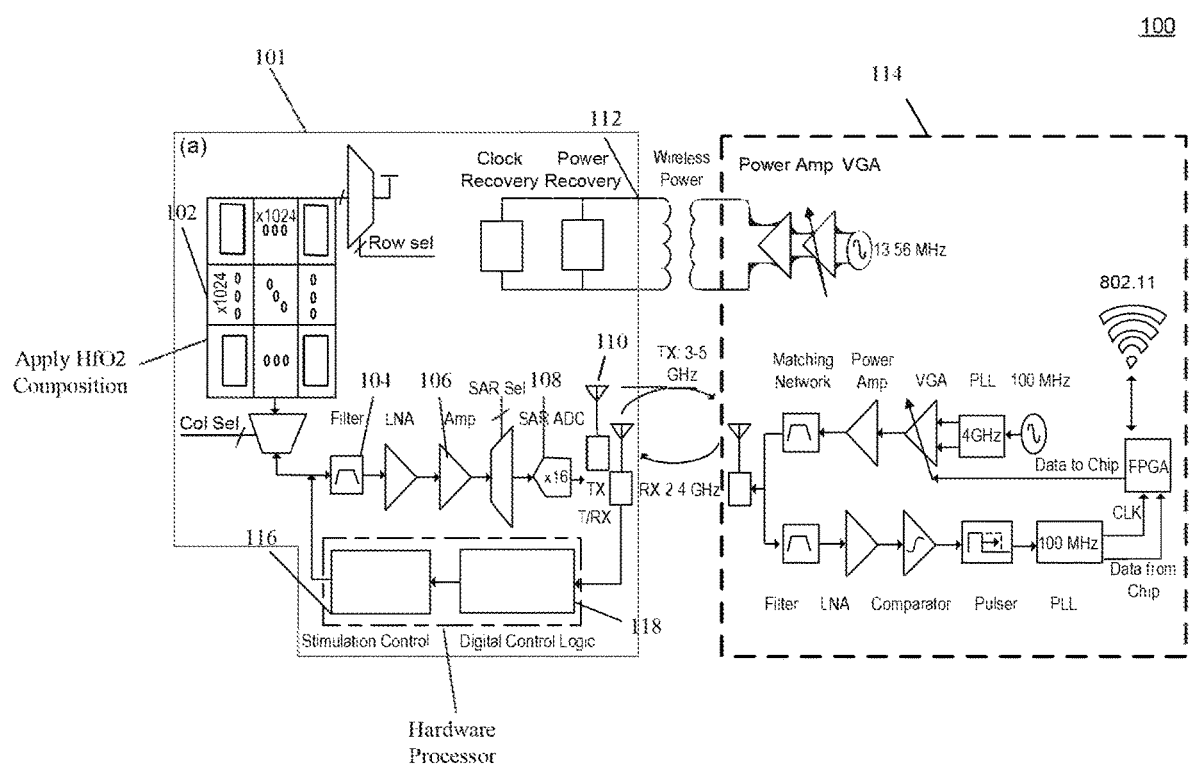
FIG. 1A illustrates an implantable, wireless, flexible CMOS surface recording system, in accordance with some embodiments of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

A fully implanted, wireless, flexible CMOS surface neural recording and stimulation device is provided herein. Specifically, in some embodiments, the device is manufactured with high electrode density and high channel count without incurring the noise-verses-density trade-offs in conventional CMOS designs. In addition, the implanted device itself will comprise a complete system: including the dense surface electrode array, the underlying CMOS integrated circuit architecture, and integrated wireless powering and telemetry. In some embodiments, this can be achieved by fully integrating circuit elements onto the chip (e.g., through monolithic integration) and by performing signal processing in the digital domain to signal recordings obtained by the device. In some embodiments, the device can be manufactured with a small form factor, which will permit implantation under the skull with no wires or connections. In some embodiments, the device can displace a volume of only 6.25 mm$^3$, while covering a significant brain surface area of 625 mm$^2$.

For example, FIG. 1A shows a circuit diagram of system 100 including a fully implanted, wireless, flexible CMOS surface recording device 101 and relay station 114. Specifically, in some embodiments, device 101 includes an electrode array 102 that is implanted in the region of interest (e.g., brain), in order to detect the desired signals. For example, device 101 can be implanted in the visual cortex to significantly improve quality of life for people suffering from blindness. Specifically, in many instances, electrical stimulation of the human visual cortex using devices of 100 or less electrodes can yield the perception of small spots of light, known as phosphenes. In some embodiments, the small feature sizes and massive scale of device 101 can provide the opportunity for patients to perceive and discriminate complex patterns at higher resolutions.

In some embodiments, device 101 includes band-pass filter 104 that provides antialiasing for the subsequent digitization of the recorded signals as well as initial noise reduction from potential recording noise resulting from the electrode array 102. In some embodiments, device 101 includes one or more amplifiers 106 to increase the power/amplitude of the recorded signals prior to performing analog-to-digital conversion using an analog-to-digital converter (ADC) 108.

For example, upon recording and conditioning the analog signal, the recordings from the electrode are digitized through the use of low-power analog-to-digital converters (ADC) 108. In some embodiments, a dedicated ultra-low power ADC is provided for each channel in the block currently being addressed. In some embodiments, time-division multiplexing in conjunction with an ADC that samples at a much faster rate that allows multiple channels to share a single ADC can be provided. This can allow for fewer ADCs at the expense of power. In some embodiments, a successive-approximation register (SAR) or pipeline ADC architecture can be used. These architectures are feasible since relatively low sampling rates are required for individual channels.

Furthermore, in some embodiments, device 101 includes a wireless power circuit 112 to ensure that the implanted device and relay station 114 are powered. In some embodiments, device 101 can be powered via batteries, capacitors, energy harvesting circuits or any other suitable combination thereof. In some embodiments, device 101 can include additional control logic devices for controlling operations of device 101. For example, device 101 can include a stimulation control logic unit 116 for controlling the electrode array 102 when it is operating in a stimulation mode. Stimulation control logic unit 116 can provide commands to one or more blocks of electrode array 102 associated with a stimulation pattern in a region of interest. In addition, device 101 can include digital control logic unit 118 that generates control commands for the overall operation of device 101. For example, digital control logic unit 118 can determine the switching of the operation of electrode array 102 from a sensing/recording operation mode to a stimulation operation mode. In some embodiments digital control logic unit 118 can automatically detect the appropriate switching times and associated parameters for electrode array 102. In some embodiments, switching can be performed manually or in any other suitable manner.

Furthermore, relay station 114 of system 100 can wirelessly exchange data and power with device 101. In some embodiments, relay station 114 is a transceiver that sits outside the body positioned against the head in a cap or in any other suitable wearable manner and has a small form factor. In some embodiments, relay station 114 transmits data from device 101 to a base-station (not shown) for off-chip analysis. In some embodiments, base-station can be either a computer, a smart phone, a server or any suitable hardware processor. Further, relay station 114 can operate at a high-power budget since it is located outside the body and can be easily heat-sunk. For example, in some embodiments, relay station 114 can incorporate an 802.11n chipset and a 3.7-V, 4.2-Amp-hour lithium-ion battery thus consuming approximately 15 W when active and about 50 mW in standby, giving about 1 hour of activity on a battery charge. In addition, with the above parameters, total weight for the relay station 114 (e.g., wireless transceiver) will be about 5 g, dominated by the battery and the total board size will be approximately 100 cm². In some embodiments, the link between the relay station 114 and other 802.11n wireless devices can be secured using the WPA2 standard or any other suitable encryption standard. In addition, in some embodiments, the link between the relay station 114 and device 101 can be secured with secret keys, but the very short-range nature of this link can make this unnecessary.

In addition, in some embodiments, wireless power circuit 112 can be a wireless RF link operating in near-field at 13.56 MHz, delivering ~300 mW to power both its stimulation/recording circuitry and two far-field impulse-radio ultra-wide-band (IR-UWB) microwave data links operating at a rate of 100 Mb/s. In some embodiments, the data downlink from the relay station 114 to device 101 shares the same antenna as the uplink with an on-off-keying modulation approach achieving a data rate of 50 Mb/s. In some embodiments, the external transceiver can be battery powered and can communicate to the outside world using, for example, the 802.11n protocol.

Figure 1B:
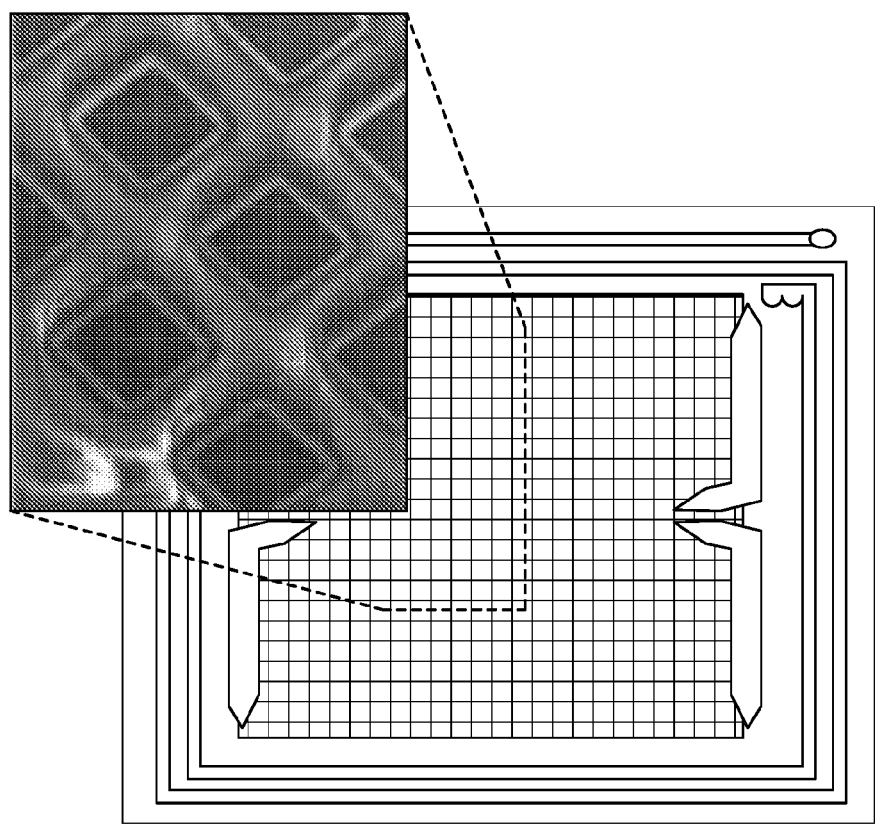
FIG. 1B illustrates a fabricated microelectrode array in accordance with some embodiments of the disclosed subject matter.

FIG. 1B shows a flexible, fabricated microelectrode array 102 integrated into the CMOS chip. In some embodiments, microelectrode array 102 employs non-penetrating, high-density electrodes that can perform in a dual operation mode. For example, in some embodiments, microelectrode array 102 can provide capacitive sending and stimulation of the desired region, which allows full dielectric encapsulation of electrodes for long-term stability. In some embodiments, use of conducting polymers or high surface area coatings can yield capacitances as high as 60 fF/$\mu m^2$ for microelectrode array 102. In addition, fabricated microelectrode array 102 can provide non-penetrating electrode arrays to channel counts more than three orders of magnitude higher than the current state-of-the-art (e.g., to realize channel/electrode density exceeding 2500 electrodes/mm²), through use of active CMOS arrays.

Figure 1C:
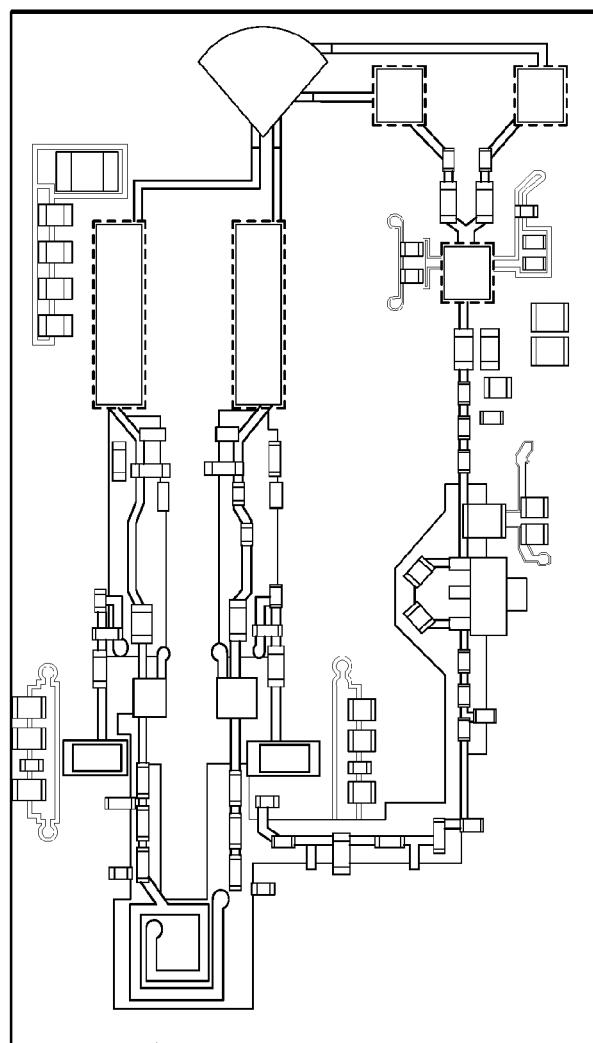
FIG. 1C illustrates a relay station mounted outside a person's head in accordance with some embodiments of the disclosed subject matter.
Figure 1C:
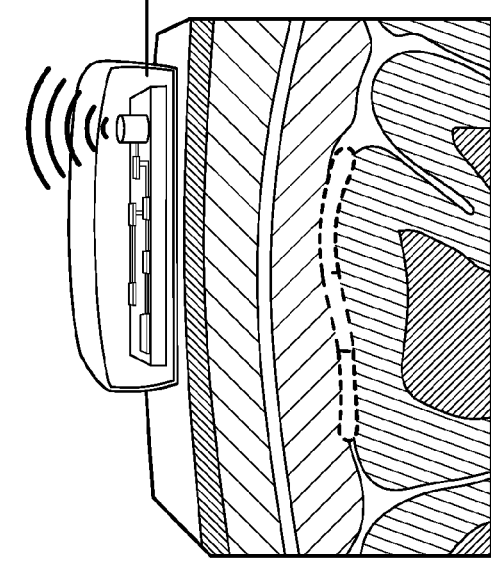

Moreover, FIG. 1C shows a schematic of relay station 114 that can provide power to the CMOS chip and relay data both to and from the implanted device 101. Specifically, in some embodiments, in order to allow for the device to be fully implantable, antennas 110 can be fully integrated onto the flexible CMOS chip. For example, in some embodiments, one set of antennas can operate to receive power at a lower carrier frequency (13.56 MHz) and another set of antennas 110 can be used to transmit and receive digital information using an ultra-wide band link at a center frequency of 4 GHz. In some embodiments, the two sets of antennas can operate two decades apart as to reduce interference and maintain fidelity of the transmitted signals. In addition, in some embodiments, such configuration allows for no battery to be incorporated into the implanted device.

Furthermore, due to certain design restrictions associated with the region of implantation, it is advisable for power dissipation by an implanted device in the brain to be kept below 500 μW/mm2, to insure local tissue heating below 1° C. In some embodiments, in order to isolate power and data transfer signals, a multi-antenna solution can be employed. Specifically, antennas can be completely integrated onto the CMOS die. As mentioned above, in some embodiments, these power and data links operate over two decades apart in frequency to avoid interference. For example, for power transfer, the ISM band at 13.56 MHz with a coil that completely surrounds the outer circumference of the integrated circuit can be used. In some embodiments, a series resistance in the receiving coils can be reduced by the use of centimeter-scale, wide metal to limit losses.

In some embodiments, for high rate data transfer off the chip, ultra-wide-band (UWB) techniques can be used. For example, Impulse radio (IR) UWB can provide a simple, digital-circuit-style implementation to provide data rates as high as 500 Mb/s. In some embodiments, an IR-UWB system can be centered at 4 GHz with a 900-MHz bandwidth (3.1 GHz to 4.9 GHz). Specifically, this bandwidth allows use of 1.1 ns transmission pulses with 10 ns of reset time before the next pulse. In some embodiments, a wideband, differential dipole antenna can be used to transmit the data to the relay station 114. For example, a '1' can be encoded using a 1-ns burst of a 4 GHz square wave, and a '0' can be encoded with silence. In some embodiments, bursts are sent every 10 ns, corresponding to a data rate of 100 Mb/s. Further, differential edge combining can be used to generate the UWB signal. In some embodiments, a 125 ps pulse is generated on the rising edge of a '1' using an edge detector circuit and a series of matched delay elements can provide 8 edges, spaced about 125 ps apart. In such cases, the delayed edges are combined with a series of differential drivers to provide the current to the antennas 110 and 116.

In some embodiments, the incoming data from the CMOS device 101 is received at the relay station 114 with a matched antenna. Specifically, the received UWB modulated data can be filtered and rectified to extract the envelope. In some embodiments, the filtered signal can be buffered with a low noise amplifier and fed into a comparator. Since the modulation scheme is impulse radio based, the comparator converts the signal into the digital domain. The digital signal pulses can then be elongated before driving a clock and data recovery circuit.

Figure 1D:
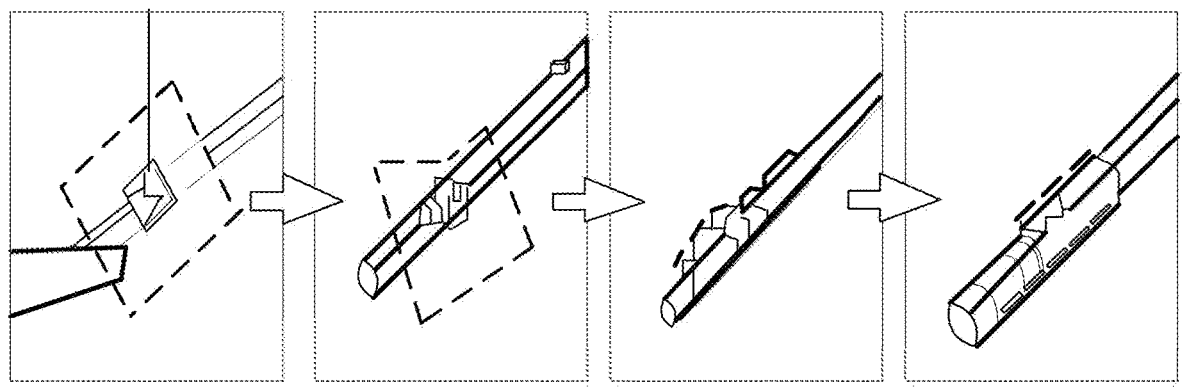
FIG. 1D illustrates a fabricated thin flexible CMOS integrated recording and stimulation device, in accordance with some embodiments of the disclosed subject matter.

FIG. 1D shows a thin chip integrating the above discussed elements and fabricated using both mechanical and chemical process in accordance with the disclosed subject matter. As shown in FIG. 1D, thinned and flexible device 101 can conform to a region of interest so as to ensure efficient operation during recording and stimulation. Indeed, as discussed above in reference to FIG. 1B, integrated microelectrode array 102 can provide sensing and stimulation of the desired region. Specifically, the use of active CMOS microelectrode arrays, can realize densities three orders of magnitude greater than existing arrays. For example, through the use of modern CMOS processes, a density in excess of 2500 electrodes per square millimeter can be achieved.

Figure 2A:
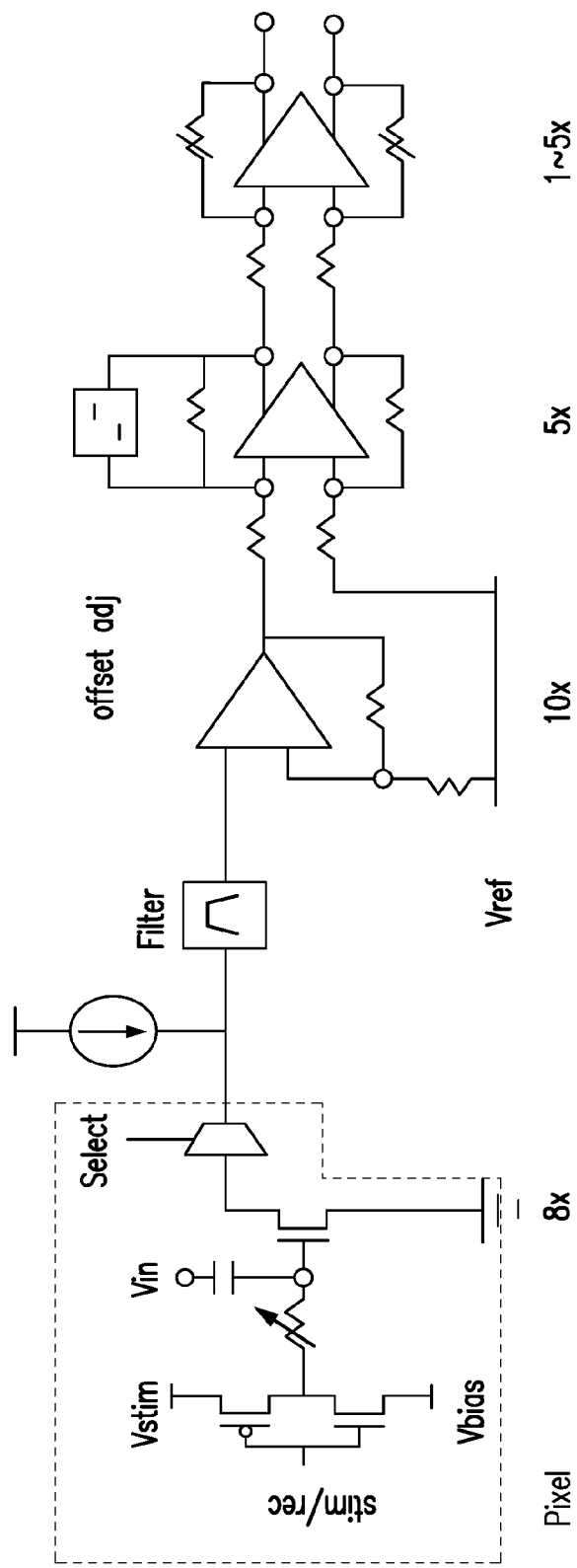
FIG. 2A illustrates a circuit diagram of an element in the microelectrode array in accordance with the system of FIG. 1A.

Additionally, in some embodiments, these electrodes are non-penetrating, allowing for the realization of a practical device for clinical applications. In some embodiments, as discussed above, microelectrode array 102 enables dual operation mode providing electrical recording and patterned stimulation. For example, in some embodiments, capacitive sensing and stimulation, which allows for full dielectric encapsulation of electrodes for long-term stability, can be used to record and stimulate from the surface of the brain while keeping the device hermetically sealed. In some embodiments, conducting polymers or high surface area coatings can be used to increase the capacitances for these electrodes FIG. 2A illustrates a circuit diagram of the stimulation and recording circuit of microelectrode array 102. Specifically, in some embodiments, electrodes are addressable in blocks on the order of 1,024 electrodes (or some binary multiple thereof) and can be programmed to stimulate and record within those blocks in an arbitrary pattern determined by stimulation control unit 116 and digital control logic unit 118. Furthermore, in some embodiments, multiplexing techniques can be provided in order for a high amplifier density to be realized at low power. As discussed above, in some embodiments, amplifiers 106 are integrated both before and after multiplexing to boost the signal before data conversion. In some embodiments, microelectrode array 102 can be a 65,536-channel amplifier chip that can support a per-electrode bandwidth of 10 kHz with a sample-rate of 20 kS/s when recording from the entire chip. Further, in some embodiments, unused amplifiers can be powered off when not "selected" in a given time interval allowing for a power savings result. In some embodiments, each effective recording channel can have a variable gain up to 80 dB and can deliver an input-referred noise of 7 µV rms over a 100 Hz to 10 kHz bandwidth (and a 22 µV rms input-referred noise over a 1 Hz to 400 Hz bandwidth, as suitable for neuronal Local Field Potential monitoring).

Figure 2C:
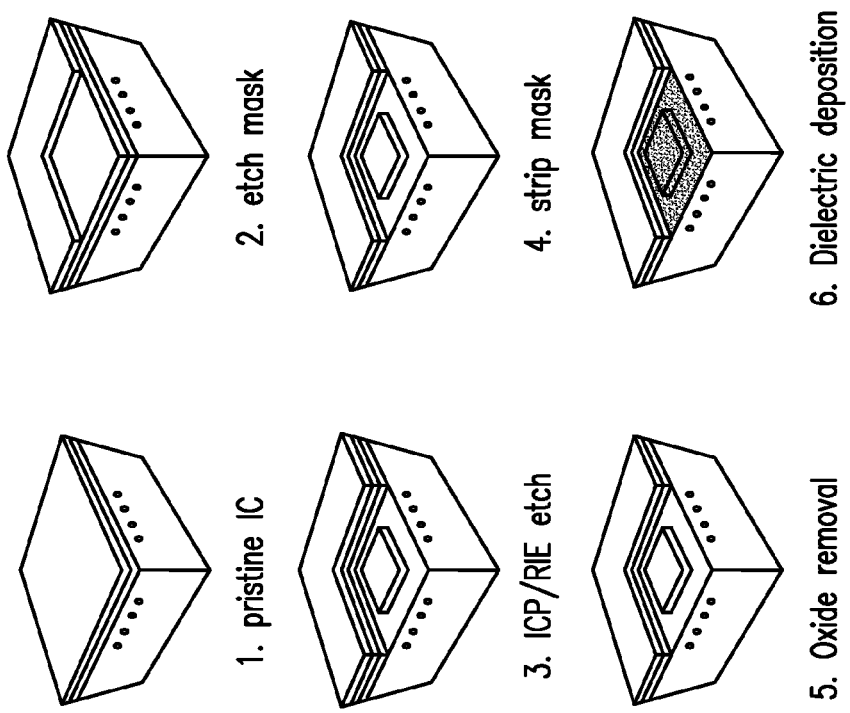
FIG. 2C illustrates post-processing of the pixel array of FIG. 2B in accordance with some embodiments of the disclosed subject matter.
Figure 2B:
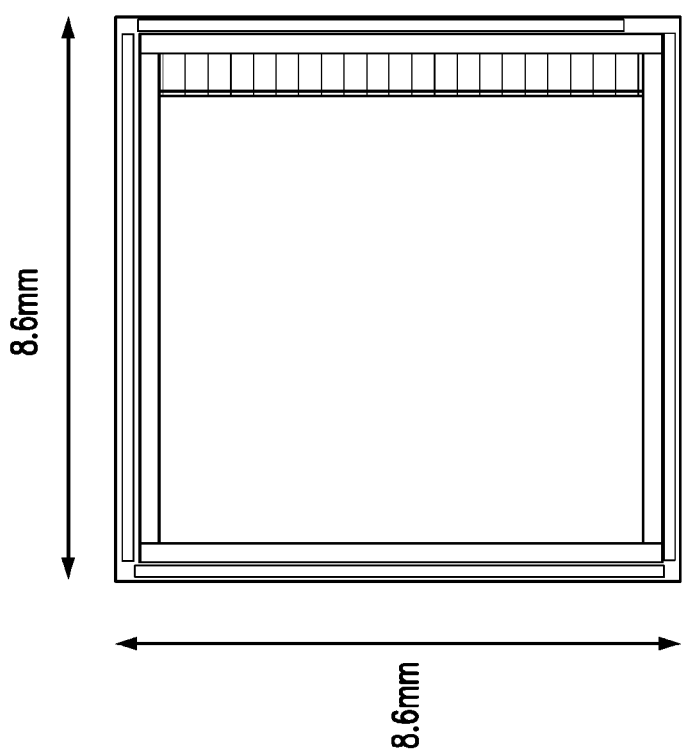
FIG. 2B illustrates a fabricated pixel array in accordance with the system of FIG. 1A.
Figure 2D:
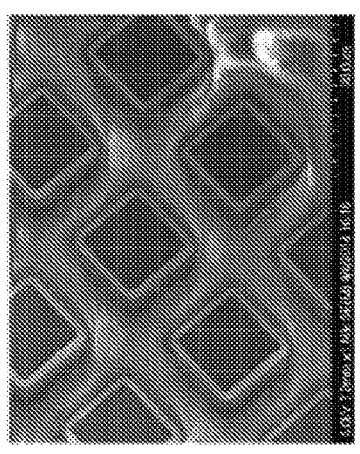
FIG. 2D illustrates an electrode array grid in accordance with the pixel array of FIG. 2B.
Figure 2E:
FIG. 2E illustrates an enlarged picture of an electrode contained in the electrode array of FIG. 2D.

FIG. 2B illustrates a picture of a fabricated microelectrode 65,536-pixel array grid 102 using electron microscopy. FIGS. 2D and 2E illustrate an enlarged view of a single electrode fabricated on the pixel array of FIG. 2B. In some embodiments, the recording and stimulating electronics can be based on a 65,536-channel stimulating and recording chip integrating the 65,536-pixel array grid. In some embodiments, this chip can operate as a CMOS imager. Specifically, in some embodiments, the CMOS chip can perform sampling and time-multiplexing in the front-end. Furthermore, in some embodiments, unused amplifiers can be powered off when not "selected" in a given time interval, yielding significant power savings (e.g., a chip power consumption of 0.33 µW/channel).

In addition, in some embodiments, a 0.13-µm technology node can be employed to shrink the individual pixel size to 20 µm by 20 µm. As a result, using pixel level electronics that fit within this 400 µm2 pixel area can lead to input-referred noise levels of approximately 6 µV rms at 3-kHz bandwidth. For example, in some embodiments, the first stage of pixel-level amplification can be accomplished with only three transistors per pixel, one of which can be used for multiplexing. These front ends are multiplexed into one of several parallel signal-processing chains, each of which can handle up to 4000 pixels. In some embodiments, on-chip 8-bit SAR ADCs at a sample rate of 20 kHz per pixel can be used for data conversion for providing a significant reduction in power while preserving signal integrity.

FIG. 2C illustrates post-processing for fabricating an integrated CMOS flexible microelectrode array 102. Specifically, in some embodiments, an etch mask can be applied on a pristine integrated circuit (IC) followed by inductively-coupled-plasma (ICP)/Reactive-ion etching (RIF). In addition, a strip mask can be applied to the etched IC to perform oxide removal eliminating the passivation layer. Further, in some embodiments, backside thinning can be performed to ensure that device 101 is flexible and pliable based on specified design requirements. Finally, dielectric deposition and patterning can be employed in order to obtain the thin (e.g., less than 15 µm), flexible microelectrode array 102. For example, in some embodiments, microelectrodes 102 are post-processed with the high-k dielectric $HfO_2$ to provide a robust moisture barrier layer, that protects the powered chip from the corrosive environment in the body. As discussed above, thinned, flexible CMOS devices are provided that can become pliable when made sufficiently thin. Specifically, in some embodiments, a variety of thinning methods can be employed to support three-dimensional (3D) integration of thin silicon stacks. For example, chemical-mechanical polishing (CMP), wet etching, and dry chemical etching (DCE) can be utilized to produce a CMOS chip less than 10 µm in total thickness, giving them the necessary pliability associated with the prescribed design requirements.

In some embodiments, microelectrode array 102 can be a passive electrode array fabricated using conducting polymer-based, poly(3,4-ethylenedioxythiophene) doped with poly(styrenesulfonate) doped with poly(styrenesulfonate) (PEDOT:PSS) integrated in a 4-µm-thick parylene film. In addition, PEDOT:PSS as electrode material offers ionic and electronic conductivity (e.g., 20 µm×20 µm recording sites exhibit 30 kΩ impedance at 1 kHz, as well as biocompatibility and chemical stability). In some embodiments, iridium oxide can be used for fabricating microelectrode array 102 or any other suitable electrode material.

Furthermore, a biocompatible, FDA approved class-6 polymer such as Parylene can be used for passivation of the chip. Parylene is a chemically inert material and can provide electrical insulator. Upon thinning, microelectrode arrays 102 possess adequate mechanical strength to be readily manipulated by the experimenter yet allow for high conformability permitting neuron-size electrodes to attain excellent electrical and mechanical contact with the curvilinear surface of the brain or any other suitable tissue. In some embodiments, microelectrode arrays 102 can be patterned from polyimide or dissolvable silk substrates, thus relying on external measurement electronics.

Figure 2G:
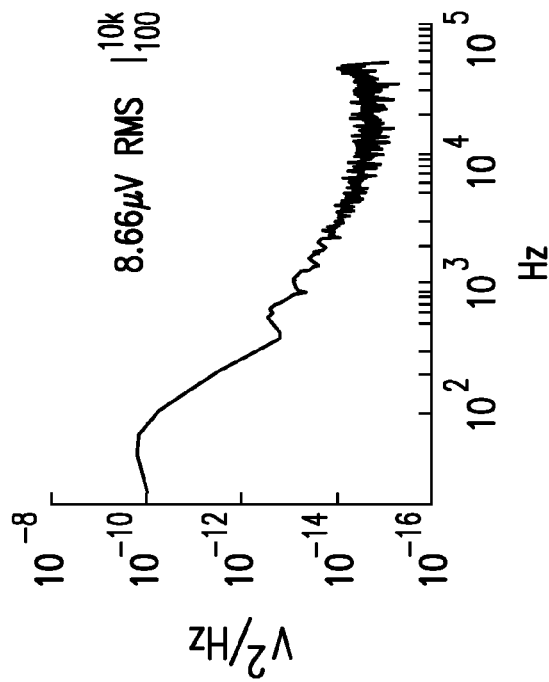
FIG. 2G illustrates a plot diagram with exemplary results for the system of FIG. 1A.
Figure 2F:
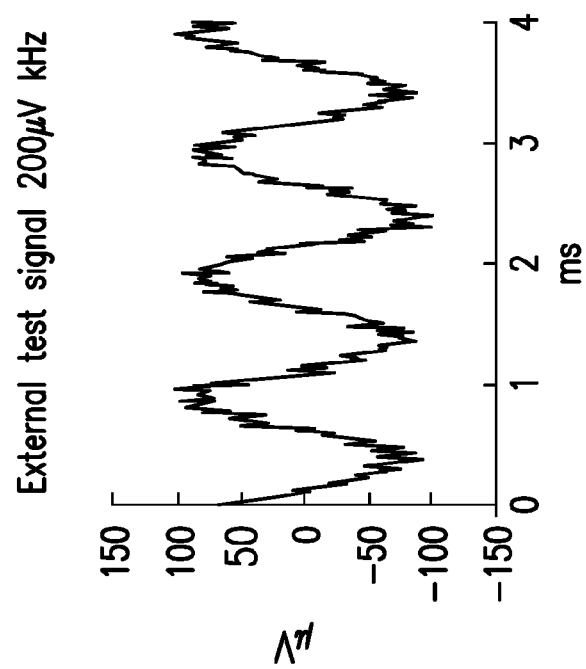
FIG. 2F illustrates a plot diagram with exemplary results when using the electrode of FIG. 2E.

FIGS. 2F-2G illustrate plot diagrams during use of the microelectrode array 102 in device 101. Specifically, FIG. 2F provides a plot diagram involving a recording of a test sinusoid signal applied to a single electrode integrated in the microelectrode array 102. Specifically, FIG. 2F illustrates a single electrode recording of microelectrode array 102 when provided with a 200 µV amplitude 1 kHz sine wave. In addition, FIG. 2G illustrates a plot diagram providing power spectral density highlighting low noise in the system of FIG. 1A.

Figure 3:
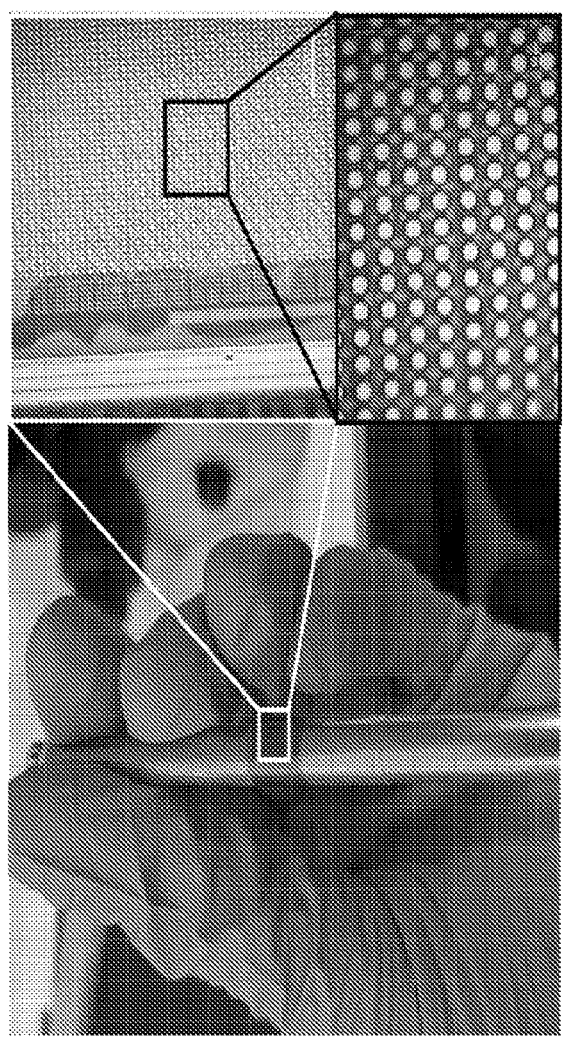
FIG. 3 illustrates an implantable, wireless, flexible, thin microelectrode array in accordance with some embodiments of the disclosed subject matter.

FIG. 3 illustrates an exemplary embodiment of a wireless, flexible CMOS surface recording device including microelectrode array 102. As illustrated, in order to make the device implantable for long-term use, the device is fabricated to displace very little volume. Specifically, the thinned chip is highly pliable and provides high degree of optical transparency (>60%), which allows for the simultaneous optical and electrical recording. As discussed above, in some embodiments, to achieve the desired design requirements the CMOS device is thinned using mechanical and chemical techniques to, for example, a total thickness of less than 15 µm providing an integrated circuit with a significantly increased mechanical compliance that can conform to the surface of the brain. In some embodiments, after thinning, a passivation layer consisting of aluminum-oxide-parylene multilayers is deposited to seal the device and make it biocompatible for implantation as discussed above in reference to FIG. 2C.

Furthermore, as shown in FIG. 3, the CMOS device 101 is rendered highly-flexible by extreme thinning so that the surface recording array is in conformation to the desired tissue e.g., pial surface of the brain. Specifically, bending stiffness for these dice, can scale roughly with the cube of the film thickness, allowing a reduction in die bending stiffness from roughly 1.76 Nm for a standard 500 um thick die to only 5 µm for a fully thinned die. As a result, the six-order-of-magnitude increase in mechanical compliance allows the device to tightly conform to the curvilinear surface of the brain.

Figure 4B:
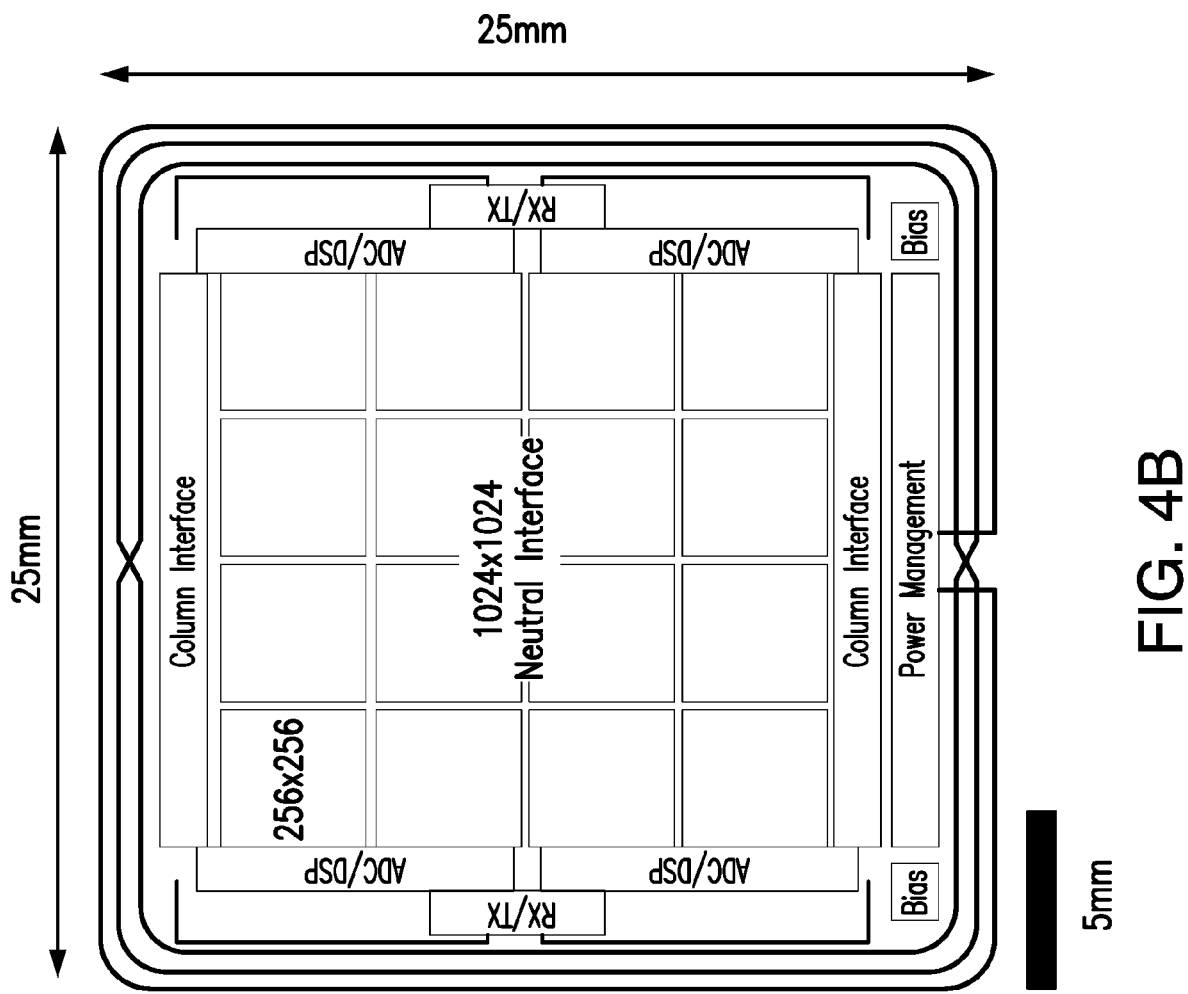
FIG. 4B illustrates an implantable, wireless, flexible CMOS recording surface device using an alternate architecture, in accordance with some embodiments of the disclosed subject matter.
Figure 4A:
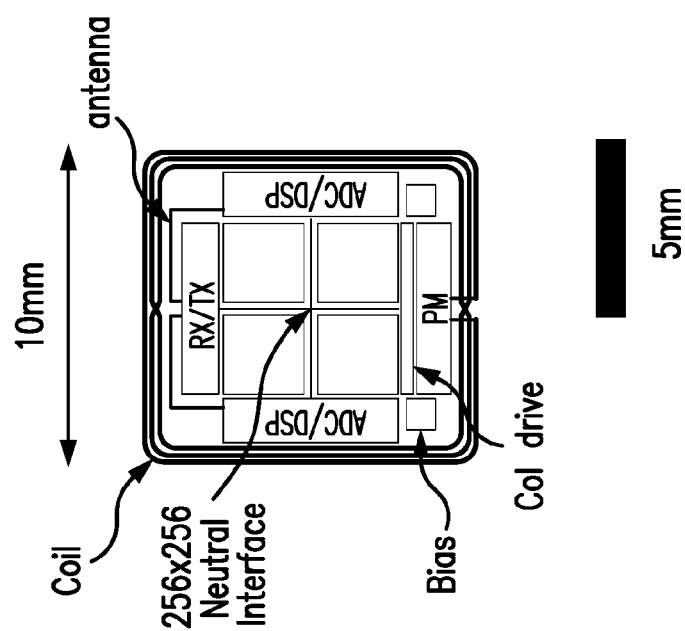
FIG. 4A illustrates an implantable, wireless, flexible CMOS recording surface device using an exemplary architecture, in accordance with some embodiments of the disclosed subject matter.
Figure 4C:
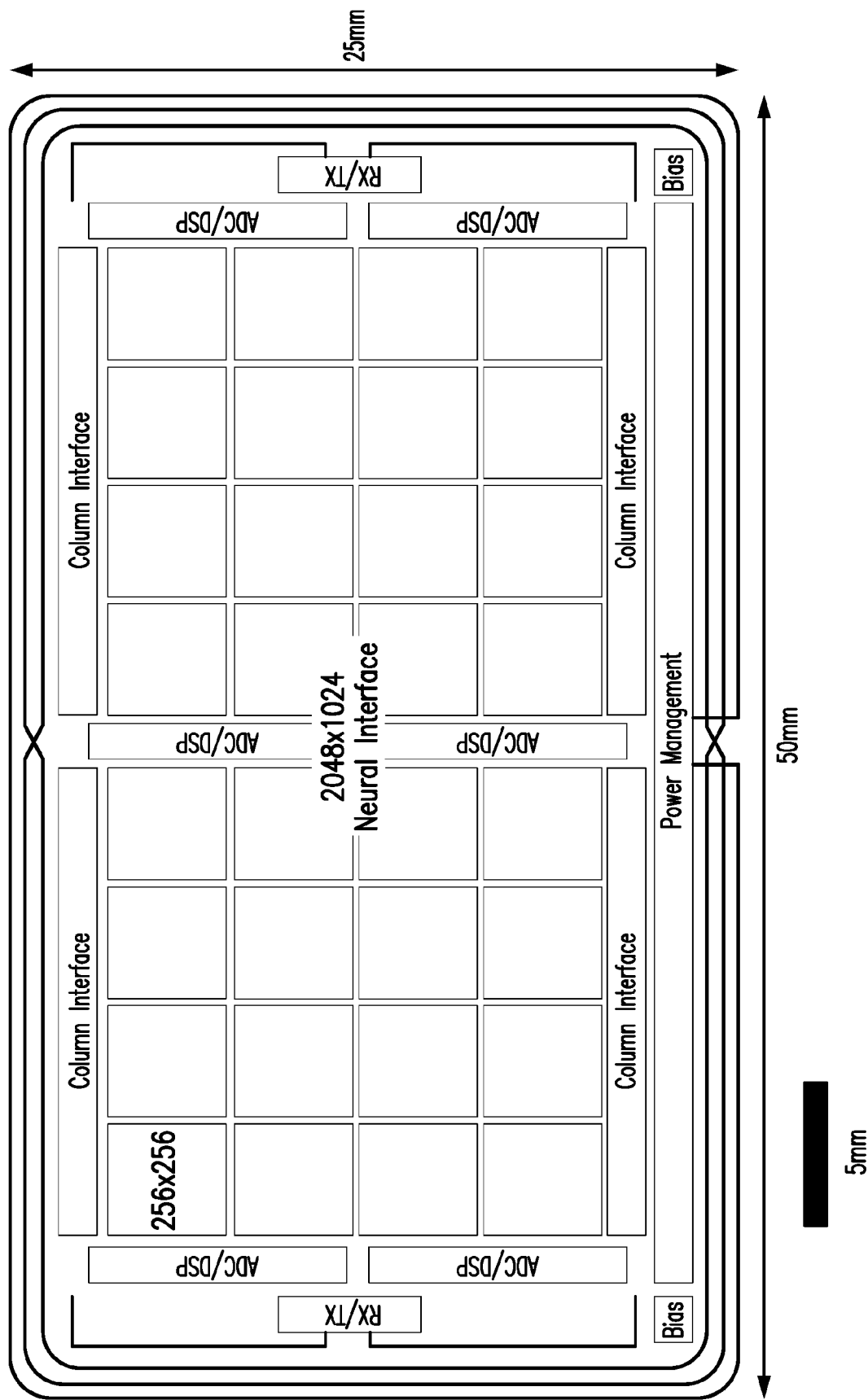
FIG. 4C illustrates an implantable, wireless, flexible CMOS recording surface device using an alternate enhanced architecture, in accordance with some embodiments of the disclosed subject matter.

FIGS. 4A-4C illustrate different manufactured architectures of a flexible CMOS surface recording and stimulation device 101. Specifically, FIG. 4A shows a CMOS recording and stimulation device 101 that is manufactured with an area of 1 cm×1 cm and has a microelectrode array 102 with 65,536 electrodes on a 25-µm pitch. Further, as discussed above, for power transfer, CMOS recording and stimulation device 101 uses the ISM band at 13.56 MHz with a coil that completely surrounds its outer circumference, as shown in FIG. 4A. In some embodiments, the power coil is designed such that it can be coupled to a single coil design at the relay station, allowing one relay station design to be used across the platform.

In addition, in some embodiments, one UWB antenna can be used for the data uplink to improve the data rate without excessively increasing complexity. Further, both the transmit (TX) and receive (RX) RF transceiver designs can use a differential dipole antenna for both RX and TX of data. In some embodiments, each antenna can be tuned to 4 GHz and can be designed to transmit 100 Mb/s of data. In some embodiments, due to the smaller reticle size, the TX/RX Antenna of device 101 using the architecture illustrated in FIG. 4A can have a hook shape but can still effectively act like a differential dipole antenna.

Moreover, for device 101 shown in FIG. 4A, the first stage of pixel-level amplification can be accomplished with, for example, only three transistors per pixel, one of which can be used for multiplexing. In some embodiments, these front ends can be multiplexed into one of several parallel signal processing chains, each of which can handle up to 4000 pixels (e.g., requiring 16 channels for device 101).

FIG. 4B illustrates an alternate architecture for flexible CMOS surface recording and stimulation device 101. Specifically, FIG. 4B shows device 101 manufactured with an area of 2.5 cm×2.5 cm including 1,048,576 electrodes on a 20-µm pitch. In some embodiments, power transfer can be accomplished using the ISM band at 13.56 MHz with a coil that completely surrounds the outer circumference of the device. For example, in such architectures, with a power budget of 315 mW, the transmitter on the relay station 114 can emit approximately 10 W, with specific absorption rate (SAR) levels expected to remain below 0.7 W/kg. In some embodiments, series resistance in the receiving coils can be reduced through the use of centimeter-scale, wide metal to limit losses.

Further, in some embodiments, device 101 illustrated in FIG. 4B can use two UWB antennas. In such cases, the large reset time can permit use of time division multiplexing to two antennas operating simultaneously and broadcasting to a single receiver on the relay station 114. These antennas can also be used to receive instructions on-chip from the relay station. Specifically, in some embodiments, the two sets of differential antennas can lead to an overall effective data rate of 200 Mb/s from the chip 101 to the relay station 114. In some embodiments, in order to limit coupling between the two pairs, time multiplexing can be implemented. In addition, in some embodiments, the on-chip length of each monopole antenna can be 4 mm, or any other suitable length based on design characteristics, which when tuned to a 4 GHz center frequency can lead to an effective wavelength of 1.6 cm, assuming a dielectric constant of $C\varepsilon=21.97$, representative of a thinned silicon resting on top of brain grey matter and directly underneath the dura and skull. Further, the effective −10 dB bandwidth using the above parameters is 1.4 GHz, which is wide enough to transmit the required 100 Mb/s. In some embodiments, the TX efficiency and RX efficiency of the antenna can be approximately equal across the band at 13.4%, and the system can have an effective beam width of 87 degrees. In such cases, the antenna/transmitter gain of the system is found to be −24.6 dB and assuming a separation of 2 cm=2.5λ, and given a transmitter power of 2 dBm, the power received at the relay station 114 can be calculated to be −77 dBm, about 7 dB above the noise floor.

FIG. 4C illustrates an alternate architecture for flexible CMOS surface recording and stimulation device 101. Specifically, FIG. 4C is an enhanced platform associated with FIG. 4B that has an area of 2.5 cm×5 cm and includes a microelectrode array 102 with 2,097,152 electrodes. Device 101 using the enhanced architecture can be formed using reticle stitching of the architecture shown in FIG. 4B and can include similar design parameters.

Figure 5:
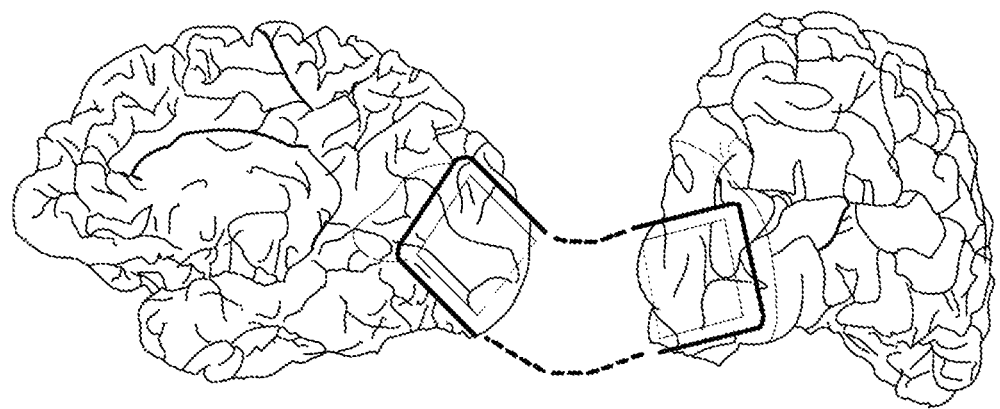
FIG. 5 illustrates a diagram of an exemplary position of implantation of the flexible CMOS integrated device of FIG. 1A, in accordance with some embodiments of the disclosed subject matter.

In some embodiments, device 101 (implemented in any of the architectures illustrated in FIGS. 4A-4C) can be implanted in a small occipital craniotomy (e.g., approximately 6 cm in maximal dimension) over the occipital cortex of one subject's hemisphere. For example, device 101 can be positioned over the surface of the occipital pole and adjacent inter-hemispheric occipital cortex, as shown in FIG. 5. Specifically, device 101 employing the architecture illustrated in FIG. 4B (e.g., with the 2.5 cm×5 cm overall size) can lie approximately with one half on the lateral surface near or over the representation of the fovea (central 2° of visual space), and the other half in the inter-hemispheric space (2-10°). In some embodiments, after implantation, the dura, skull, and scalp can be closed in anatomic fashion, and the device 101 can be completely contained within the intracranial space with no exiting wires. Upon implantation, device 101 can commence recording raw signals and/or stimulating the region of interest using microelectrode array 102. In addition, recorded signals can be relayed to relay station 114 for further transmittal to a base-station.

In some embodiments, system 100 can include a base-station for performing off-chip signal analysis of the raw signals recorded by microelectrode array 102. For example, in sensory applications, data analysis can consist of two important transforms: the signal transform, which maps neuronal activity to electrical signals recorded at the array (and, by reciprocity, permits defining spatiotemporal stimulation patterns from the massive array to target specific neurons) and the percept transform, which maps neuronal activity in subcortical layers to experiences that are both perceived and induced in the subject. In some embodiments, the signal transform can either be implemented fully in software or partially on chip 101. In addition, such signal processing should be fully automatic (requiring no user intervention) and real-time, as it will not be possible to store the data offline for subsequent analysis.

Figures 6A, 6B:
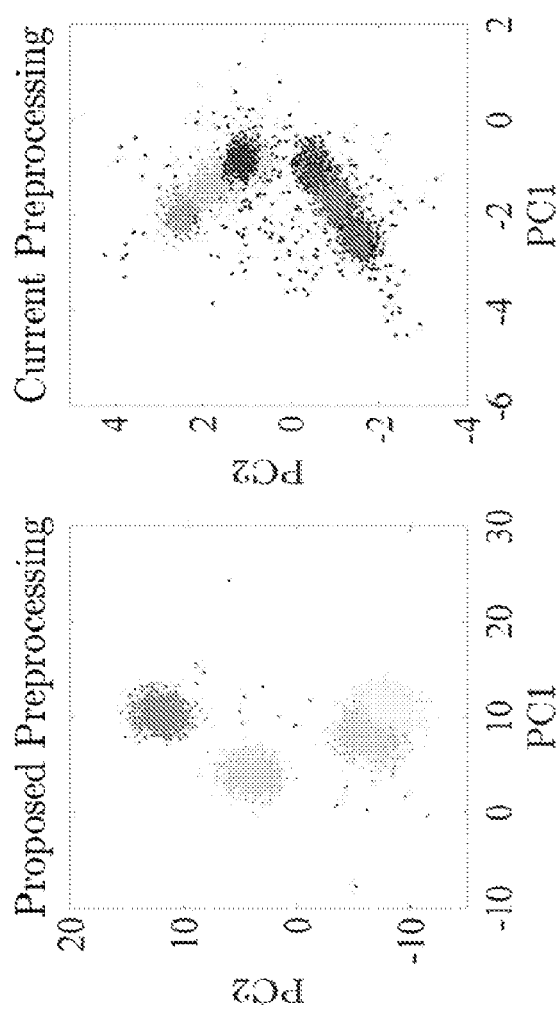
FIG. 6A illustrates a diagram of exemplary outputs using the flexible CMOS integrated device of FIG. 1A, in accordance with some embodiments of the disclosed subject matter.
FIG. 6B illustrates a diagram of alternate exemplary outputs using the flexible CMOS integrated circuit of FIG. 1A, in accordance with some embodiments of the disclosed subject matter.

In some embodiments, after filtering raw signals using bandpass filter 104 from the recording microelectrode array 102 to eliminate out-of-band information, a time-frequency dictionary-learning method can be used in order to compress non-action-potential (AP) signals for low-bandwidth transmission off-chip. In some embodiments, additional AP features can be identified during such process. For example, in some embodiments, online scalable stochastic Dirichlet process variational inference methods or any other suitable method can be used to perform clustering on highly-dimensionally-reduced representations of the spiking event waveforms as shown in FIGS. 6A-6B.

In some embodiments, multi-neuronal "collision" events can be identified, and subsequently eliminated using efficient orthogonal matching pursuit methods. In addition, Kalman tracking of the mean waveform can robustly and efficiently handle data non-stationarity. In some embodiments, the output of such analysis can provide spike times and identities, along with Bayesian measures of confidence about the timing and identity of each detected event. Furthermore, "spikes" here will be broadly defined, since in many cases these will be weaker signals than conventionally associated with AP features. In addition, the time-varying cluster means or subsampled detected spike waveforms can also be obtained, for offline model checking and validation.

In some embodiments, the computer station can be equipped with on-line software capable of learning patterns in the recorded neural data in real time. Clustering of high dimensional data can be achieved by modern Dirichlet process variational inference methods as shown in FIGS. 6A-6B. For example, by extracting features and identifying action potentials, the off-chip system can accurately correlate and investigate neural activity. In some embodiments a control feedback loop can be provided such that in response to certain events, the system 100 could be programmed to generate appropriate recording and or stimulus patterns for experiments as it observes certain motifs in the signals.

The description herein merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. An implantable neural recording and stimulation device comprising:
   a flexible and thinned complementary metal-oxide-semiconductor (CMOS) chip configured to be positioned on a pial surface of a brain; and
   an array of electrodes integrated into the CMOS chip configured to at least one of record or stimulate one or more analog signals from each of the electrodes.

2. The device of claim 1, further comprising power harvesting circuitry configured to power the CMOS chip.

3. The device of claim 1, further comprising a microcontroller coupled to the electrodes and configured to control the recording or stimulating of the one or more analog signals.

4. The device of claim 1, further comprising one or more analog-to-digital (ADC) converters coupled to the array of electrodes and configured to digitize the one or more analog signals.

5. The device of claim 1, further comprising:
   a multiplexer configured to combine the one or more analog signals into a single analog signal; and
   an analog to digital converter (ADC) coupled to the multiplexer and configured to digitize the single analog signal.

6. The device of claim 5, wherein the ADC is a Successive-Approximation-Register (SAR) ADC.

7. The device of claim 5, further comprising one or more amplifiers coupled to the electrodes and the multiplexer.

8. The device of claim 1, further comprising a first set of antennas integrated into the CMOS chip and configured to receive power.

9. The device of claim 8, further comprising a second set of antennas integrated into the CMOS chip and configured to receive and transmit one or more digital signals.

10. The device of claim 9, wherein the first set of antennas and the second set of antennas operate at least two decades apart in frequency to reduce interference.

11. The device of claim 1, wherein the CMOS chip is configured to have a thickness of 10 µm or less.

12. The device of claim 1, wherein the electrodes are deposited with a HfO2 composition.

13. The device of claim 1, further comprising an antialiasing filter coupled to the electrodes.

14. The device of claim 1, wherein a back side of the device is passivated with parylene, silicon dioxide, or both.

15. A system for neural recording and stimulation, comprising:
    an implantable neural recording and stimulation device comprising:
       a flexible and thinned complementary metal-oxide-semiconductor (CMOS) chip configured to be positioned on a pial surface of a brain; and
       an array of electrodes integrated into the CMOS chip configured to at least one of record or stimulate one or more analog signals from each of the electrodes;
    external relay circuitry communicatively coupled to the implantable neural recording and stimulation device and configured to wirelessly power and transmit one or more signals from the implantable neural recording and stimulation device; and
    a hardware processor communicatively coupled to the external relay circuitry and configured to process the transmitted one or more signals.

16. The system of claim 15, wherein the external relay circuitry comprises a transceiver configured to transmit one or more signals from the implantable neural recording and stimulation device.

17. The system of claim 15, wherein the external relay circuitry further comprises a controller configured to control the implantable neural recording and stimulation device.

18. The system of claim 17, wherein the controller is configured to select an operation mode for one or more blocks of electrodes contained in the array of electrodes.

19. The system of claim 18, wherein the selected operation mode is a stimulation mode and wherein the controller generates one or more commands for patterned stimulation using the one or more blocks of electrodes.

20. The system of claim 18, wherein the selected operation mode is a sensing mode using the one or more blocks of electrodes.

21. The system of claim 15, wherein the hardware processor is configured to detect one or more multi-neuronal events and compute a set of associated parameters.

22. The system of claim 21, wherein the hardware processor is further configured to generate clusters of the set of parameters and identify the one or more detected multi-neuronal events.

* * * * *